United States Patent
Higgins (10) Patent No.: US 9,955,959 B2
(45) Date of Patent: May 1, 2018

(54) ROTATING RETRACTOR ARM

(71) Applicant: Boss Instruments, LTD, Gordonsville, VA (US)

(72) Inventor: Sean W. Higgins, Richmond, VA (US)

(73) Assignee: BOSS Instruments, LTD, Gordonville, VA (US)

( * ) Notice: Subject to any disclaimer, the term of this patent is extended or adjusted under 35 U.S.C. 154(b) by 546 days.

(21) Appl. No.: 14/633,916

(22) Filed: Feb. 27, 2015

(65) Prior Publication Data

US 2015/0250467 A1    Sep. 10, 2015

Related U.S. Application Data (60) Provisional application No. 61/948,368, filed on Mar. 5, 2014.

(51) Int. Cl.
   *A61B 17/02*    (2006.01)
   *A61B 17/00*    (2006.01)

(52) U.S. Cl.
   CPC ........ *A61B 17/0206* (2013.01); *A61B 17/025* (2013.01); *A61B 2017/00473* (2013.01)

(58) Field of Classification Search
   None
   See application file for complete search history.

(56) References Cited

U.S. PATENT DOCUMENTS

| | | | |
|---|---|---|---|
| 4,537,085 A | 8/1985 | Valentine | |
| 4,651,969 A | 3/1987 | Dowdall | |
| 4,780,171 A | 10/1988 | Byerley | |
| 5,036,753 A | 8/1991 | Ostrand et al. | |
| 5,108,073 A | 4/1992 | Adachi | |
| 5,199,419 A | 4/1993 | Remiszewski et al. | |
| 5,471,910 A | 12/1995 | Sager | |
| 5,572,967 A | 11/1996 | Donaldson, Jr. | |
| 6,007,047 A | 12/1999 | Phipps | |
| 6,860,167 B2 | 3/2005 | Schmidt et al. | |
| 7,318,817 B2 | 1/2008 | Hamada | |
| 7,435,219 B2 | 10/2008 | Kim | |
| 7,537,565 B2 | 5/2009 | Bass | |
| 7,935,053 B2 | 5/2011 | Karpowicz et al. | |
| 7,946,982 B2 | 5/2011 | Hamada | |
| 8,296,998 B2 | 10/2012 | Stull | |
| 8,602,984 B2 | 12/2013 | Raymond et al. | |
| 8,636,656 B2 | 1/2014 | Nichter et al. | |
| 2010/0081885 A1 | 4/2010 | Wing et al. | |
| 2011/0301423 A1 | 12/2011 | Koros et al. | |

(Continued)

FOREIGN PATENT DOCUMENTS

EP    1 949 860 B1    3/2010

*Primary Examiner* — David H Willse
*Assistant Examiner* — Javier Blanco
(74) *Attorney, Agent, or Firm* — Whitham, Curtis & Cook, P.C.

(57) ABSTRACT

A rotatable arm is provided which provides an ability to rotate a working end of an instrument such as a surgical retractor. Rotation of a key hub transfers torque to a drive hub which causes an extension or retraction of a lead screw along a center axis of the rotating arm. The extension or retraction forces a drive pin to bear against sides of helical slots of a driven tip, producing a rotation of the driven tip along a pitch line of the helical slots. The driven tip is connected to the working end such that the two rotate together. The rotatable arm has a low profile, a non-reversible torque transmission, and may be hermetically sealed.

12 Claims, 6 Drawing Sheets

(56) References Cited

U.S. PATENT DOCUMENTS

2012/0182134 A1 7/2012 Doyle
2012/0239010 A1 9/2012 Shelton et al.
2012/0245432 A1 9/2012 Karpowicz et al.
2012/0265095 A1 10/2012 Fiebig
2013/0015382 A1 1/2013 Thorpe et al.

ROTATING RETRACTOR ARM

CROSS-REFERENCE TO RELATED APPLICATIONS

This application claims the priority of U.S. Provisional Patent Application No. 61/948,368, filed Mar. 5, 2014, the complete contents of which are herein incorporated by reference.

FIELD OF THE INVENTION

The invention generally relates to arms or extensions of medical devices such as but not limited to surgical retractors. More particularly, the invention relates to arms having the functionality to rotate working ends of a medical device.

BACKGROUND

During typical surgical procedures, an opening in the tissue is created and then held open using a retractor, thereby allowing the surgeon to access the tissue(s) being treated. There are numerous designs and styles of retractors which are used for various surgical procedures. In all cases, preventing unnecessary injury to the patient is desirable. Trauma to the patient can be reduced by creating a smaller incision in the tissue. The employment of surgical techniques and accompanying instruments that reduce the size of the incision, and in-turn damage to the surrounding tissues, is generally referred to as "minimally invasive surgery" (MIS). One of the drawbacks to MIS procedures is that it forces the surgeon(s) to perform the complex and critical tasks of the surgery in a reduced work space.

Figure 1:
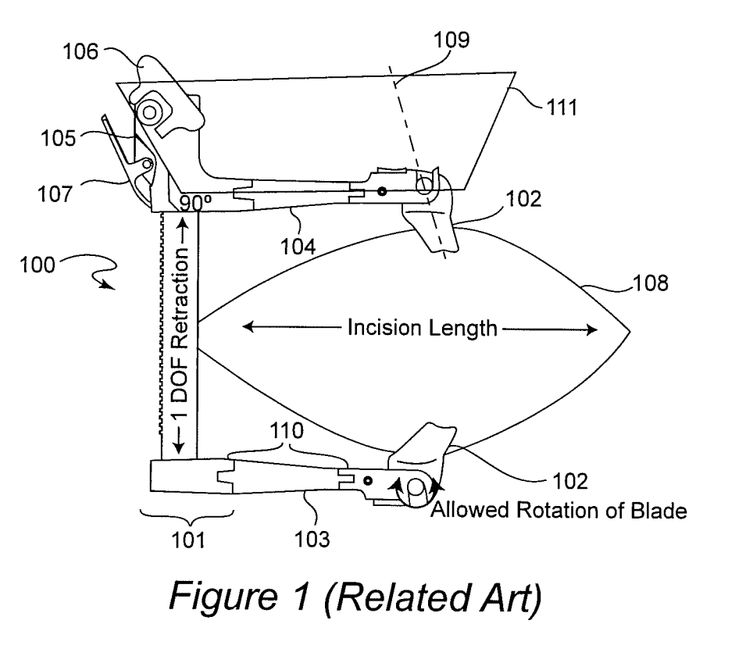
FIG. 1 shows a typical retractor frame from a top view, looking down into an incision.

Special surgical instruments have been developed to reduce the negative effects of working in a reduced space including, for example, retractor 100 shown in FIG. 1. There is a wide array of surgical retractors that use a frame 101 to which various retractor blades 102 or other tissue manipulating implements are affixed. The frame 101 is comprised of a basic rack and pinion mechanism that both separates and secures the retractor arms 103 and 104. The rack and pinion system, having a fixed hinge point on one end of the toothed rack, as well as the carriage 105 that travels along the rack and contains the pinion gear, rotated by a knob 106, and locked in position by a pawl mechanism 107, are commonly used by many providers of surgical retractors. This style of retractor is typically oriented with the rack perpendicular to the long axis of the patient's body so that tissue is separated in the medial-lateral direction. Therefore, it is commonly referred to as a "transverse" retractor. From the initial hinge points on the fixed end and carriage, moving towards the tip, changes in the design begin to appear depending on the application. Different arms are made to attach blades or hooks for separating tissue, attaching to screws to separate vertebrae, and many other applications. However, this standard frame design is employed on all of these retractor systems despite the varying working ends (e.g., blades 102).

The frame 101 supports the arms 103 and 104 which hold the retractor blades 102 in place. The blades 102, in turn, hold back the tissues once inserted into the incision 108. In transverse retractor systems, the tissue is spread apart using the rack and pinion mechanism on the frame 101 that allows for one degree-of-freedom (DOF) movement to facilitate the dilation. In many cases, the retractor blades 102 are allowed to rotate along their long axis 109 (perpendicular to the incision 108) to align with the contacting tissue. Furthermore, the arms 103 and 104 which connect the retractor blades 102 to the frame 101 can include a series of hinge points 110 allowing them to articulate in a manner that allows the device to conform closer to the skin. Typically, the long axis 109 of the blade(s) is constrained to motion residing in a single plane 111 relative to the frame 101 while facilitating the primary tissue separation.

Figure 2:
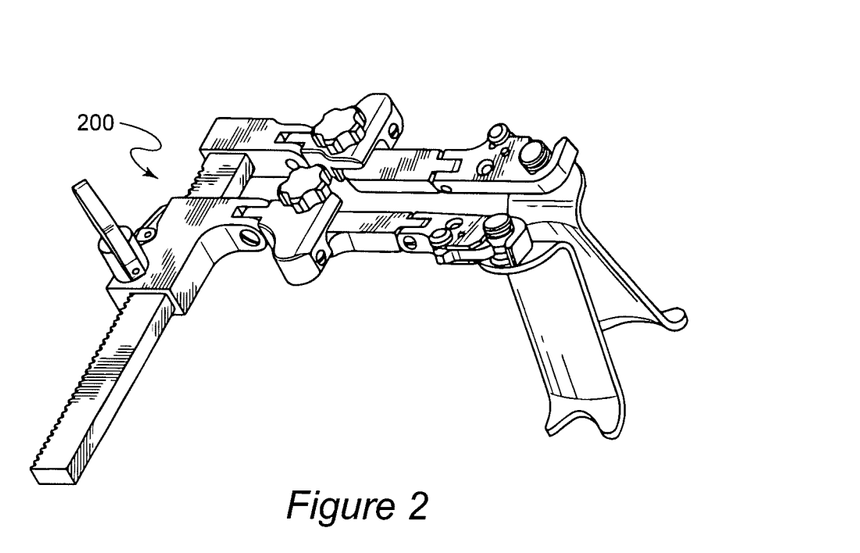
FIG. 2 shows a retractor frame from a front prospective view showing the added DOF with the "toe in" effect which allows the long axis of the retractor blade to depart from the constraining plane for secondary retraction.

Some mechanisms have been developed to provide an additional DOF to the blades of a retractor, facilitating a secondary angular direction of tissue retraction. FIG. 2 shows an example of this out of plane rotation for both blades of a retractor 200. This added DOF allows the arm(s) that secure the retractor blades to rotate outwards in a manner such that the proximal (to the patient) tip(s) of the retractor blades separate further from each other. This added rotation of the retractor arm creates a "toe in" effect at the blade (into the tissue), which displaces tissue without the need to enlarge the incision. This is desirable because the size of the incision (at the surface of the skin) is not noticeably increased; thereby reducing trauma while increasing the working space at the surgical target site.

Existing mechanisms for providing the "toe in" effect for the working ends of a retractor have numerous undesirable qualities. For example, U.S. Pat. No. 7,537,565 discloses a retractor 200 (FIG. 2) that includes a mechanism whereby a raised knob is turned to drive a screw that separates two otherwise flush metal surfaces. The separation forms an angle and gap between the surfaces which corresponds with the "toe in" angle of rotation for the blade. This mechanism is bulky for retractors, where minimal size and a low, conforming profile relative to the incision on the surface of the patient's exterior are highly desired if not required. Furthermore, the mechanism is entirely exposed to the surgical environment, introducing problems with sanitizing and maintaining the instrument between uses.

SUMMARY

It is therefore an object of the present invention to achieve the "toe in" effect of surgical retractors using an alternative and improved retractor arm mechanism. The standard frame of existing retractors is modified by replacing one or more of the long, central extension arms with a new mechanized arm. This new rotatable arm includes enclosure and isolation of all of the moving components required to provide the rotation, allowing the rotation providing mechanism to be hermetically sealed. The rotatable arm allows the blade to facilitate the secondary retraction by rotating the entire working end.

The rotation is provided using a lead screw which moves a pin (i.e., a so called "drive pin") that is captured in a helical slot of the component directly connected to the working end. This rotating component having connection means to the working end is referred to herein as the "driven tip". The driven tip is mechanically limited to just rotation (e.g., prevented from axial displacement along the center axis of the rotating arm) by means of a circumferential retaining ring. The drive pin is also captured by a straight slot (e.g., supplied by the housing), which is fixed relative to the other moving components. The straight slot limits the drive pin's relative motion to two degrees of freedom: rotation about the pin's own center (longitudinal) axis and linear travel along the center axis of the rotating arm (this being the same as the long axis of the lead screw and driven tip). As the drive pin moves within the helical slot but does not itself rotate about the center axis of the arm, it forces rotation of the driven tip.

The oblique contact between the inside bearing surfaces of the helical slots in the driven tip and the surface of the drive pin divides the torsional force transmitted to the mechanism from the tissue(s) to the working end into two discrete components. There is a torsional component that is counteracted by the ends of the drive pin which are forced against the fixed walls of the straight slot. The other component is an axial force which is transmitted directly along the long axis of the lead screw. This force component is counteracted by the threaded connection between the drive hub and lead screw. This kinematic arrangement creates a binding effect which prevents the system from being unintentionally rotated by forces applied to the working end. In other words, the direction of transmission is one-way, i.e., not reversible.

A method of controlling an orientation of such a mechanized rotating arm of a surgical retractor includes rotating the drive hub in a first direction, where the rotation of the drive hub causes an extension or retraction of the lead screw along a center axis of the rotating arm. The extension or retraction forces the drive pin to bear against sides of helical slots of the driven tip and cause a rotation of the driven tip along a pitch line of the helical slots. Rotation of the drive hub is terminated once the driven tip of the retractor has rotated a desired nonzero amount (e.g., any angle more than 0 degrees up to 90 degrees). The step of rotating the drive hub is generally achieved by a concurrent step of rotating a key hub in a second direction, the key hub transferring rotational motion to the drive hub via a meshed gearing.

DETAILED DESCRIPTION

As used herein, "proximal" indicates that a portion or end of a component is nearest to the surgeon while "distal" indicates that, compared to the proximal portion or end, a portion or end is nearest to the surgical site or patient. The same reference numerals are used through the figures when referring to the same or equivalent components or structures.

Figure 3:
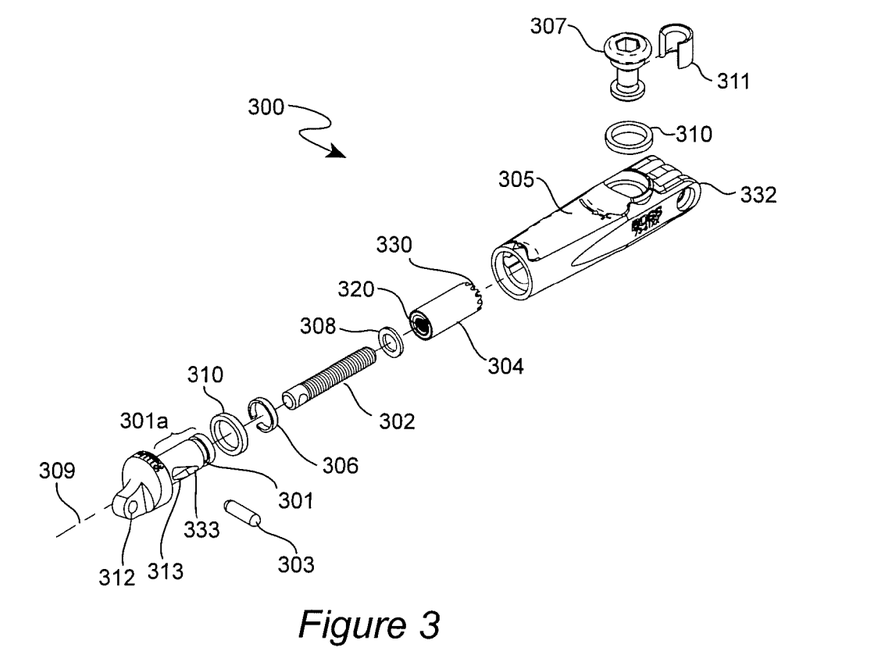
FIG. 3 is an exploded view of a rotating atm according to the invention.

Referring again to the drawings, and in particular FIG. 3, an exploded view of a rotating arm 300 (also abbreviated herein as "arm") is shown according to an exemplary embodiment of the invention. At a general level, the arm 300 includes a driven tip 301, a lead screw 302, a drive pin 303, a drive hub 304, and a housing 305. Preferably, the arm 300 also includes a retaining ring 306 and a key hub 307. Additional features may include a bearing spacer 308 or thrust bearing, seals 310, and a gap ring 311. As may be appreciated from the exploded view of FIG. 3, the long axis 309 (i.e., center axis) of the arm 300 is coaxial with the long axes (i.e., center axes) of the driven tip 301, the lead screw 302, the drive hub 304, and (the center bore of) the housing 305. For clarity and simplicity, orientation of a component will generally be made with respect to the long axis 309 of the arm 300, but it should be appreciated that it inherently implies the described orientation is also then accurate with respect to the long axes of the individual coaxial components of the arm 300.

The driven tip 301 is connectable to a working end (not shown in FIG. 3) of the surgical retractor by connection means (e.g., hinge point 312). The connection means is arranged at a distal end of the driven tip 301. A proximal portion 301a of the driven tip 301 is hollow, permitting the insertion and axial displacement of the lead screw 302 inside the driven tip 301. The proximal portion has one or more helical slots 313. In the example embodiment shown in FIG. 3, there are two matching helical slots 313 on opposite sides of the proximal portion 301a of the driven tip 301 such that the drive pin 303 is able to fully pass through the proximal portion along a line perpendicular to and intersecting with the long axis of the driven tip 301.

When the arm 300 is fully assembled, the distal end of the lead screw 302 is arranged within the hollow center of the driven tip 301 and is axially displaceable therein along the long axis of the driven tip 301. The distal end of the lead screw 302 holds the drive pin 303 (e.g., via a through hole perpendicular to the long axis of the lead screw 302). In the assembled state of arm 300, the center of drive pin 303 resides within the through hole of the lead screw 302 while both ends of the drive pin 303 pass through respective ones of the helical slots 313. Thus, portions of the drive pin 303 are disposed in the helical slots 313. Both ends of the drive pin 303 extend outside of the helical slots 313.

The drive hub 304 has gearing 330 that, when driven, causes rotation of the drive hub 304 about a center axis of the arm 300. A proximal end of the lead screw 302 has mating threads to a threaded hole 320 in a distal end of the drive hub 304. In a fully assembled state of arm 300, the lead screw is extendable and retractable from the drive hub 304 via rotation of the drive hub 304 with respect to the lead screw 302 and about the long axis of the arm 300.

According to the exemplary embodiment of FIG. 3, the rotating arm 300 further includes the key hub 307. The key hub 307 has gearing 504 (FIG. 5) that meshes with the gearing 330 of the drive hub 304 within the housing 305. The key hub 307 extends outside the housing 305 (e.g., to an outer surface of the housing 305) where it presents a user interface accessible to the human operator (e.g., the surgeon). A variety of alternative user interfaces will occur to those of ordinary skill in the art. In the embodiment of FIG. 3, the user interface is a head with a hexagonal recess, comparable to a screw head which is rotatable using an Allen wrench of corresponding size. Other configurations are also possible. For example, a simple slot rotatable with a flat head screw driver could likewise be used.

Actuation of the user interface (e.g., rotation of the screw head with an Allen wrench) provides rotation of the drive hub 304 via the meshed gearings 504 and 330. In the embodiment shown, gearings 504 and 330 are bevel gears providing a change in the operating angle of the device actuation. In this case, rotation of the key hub 307 about a first axis of rotation is transferred via the meshed gearings 504 and 330 to a rotation of the drive hub 304 about a second axis of rotation, the two axes of rotation being 90 degrees apart. The use of a common ball nosed hexagonal driver can flexibly change the external approach angle of the user interface, depending on how the hinge point(s) of the retractor frame have contoured to the patient's body, and the position of the surgeon/user. Alternatively, it may be desirable to fixedly arrange the internal gearing 330/504 between the key hub 307 drive hub 304 at some other angle other than 90 degrees if the user is going to access the retractor from another approach(es)/angle(s). Other gearing types besides bevel gears may also be used for gearing 330/504, for example a face gear.

The user interface of the key hub 307 is depressed from, flush with, or extending only a small amount above the surface of the housing 305 which surrounds the edge of the user interface. If the key hub 307 extends above the surface of the housing 305, this is preferably a maximum of a ⅓ inch protrusion. This helps maintain the advantage of the arm 300 of having a very low profile.

The gap ring 311 is placed around the narrowed section of the key hub 307 so that it's longitudinally split opening accepts the proximal portion of the drive hub 304. The gap ring fills voids around the internal components, thereby preventing lubricants from accumulating in empty space. This reduces the need for excessive application of such lubricating materials. Additionally, the reduction of open volume inside hermetically sealed devices reduces pressure differentials experienced during the sanitization process where high temperature sterilization methods are employed. Therefore, the gap ring reduces the possibility of infiltration/ exhaustion of material(s) across the seal barrier(s).

The proximal end of the housing 305 has connection means such as hinge point 332 for connecting to a retractor frame or, for example, an additional arm segment. The connection means (e.g., hinge point 332) may vary between embodiments for compatibility with various retractor frames known in the art.

The housing 305 serves the important functionality of enclosing and isolating many of the moving components of an arm 300, including the drive hub 304, the lead screw 302, the drive pin 303, and the proximal portion of the driven tip 301 from an exterior environment (e.g., a surgical site). According to an exemplary embodiment such as disclosed in FIG. 3, a rotatable arm 300 is sealed, or more preferably, hermetically sealed. An exemplary housing 305 is of unitary construction (manufactured as a single piece), but alternative embodiments may have a housing composed of a plurality of joining pieces. In FIG. 3, housing 305 has two openings: one for accessing the user interface of the key hub 307 and one permitting the distal end (i.e., head) of the driven tip 301 to sit outside the housing 305 while the proximal portion 301a is enclosed within. The exemplary arm 300 is hermetically sealed, including seals 310 at all openings to the housing 305. As a result, lubricants or other mechanical fluids may be provided within the housing 305 without a risk of the exposure to a patient's tissues. Furthermore, the arm 300, being hermetically sealed, allows for easier and more reliable cleaning between uses (e.g., reprocessing between operations), thereby reducing the risk of exposing patients to potentially hazardous materials (e.g., bioburden and microorganisms).

Furthermore, the housing 305 is involved in the prevention of axial displacement between the driven tip 301 and the drive hub 304. This guarantees that extending the lead screw 302 from the drive hub 304 will cause the distal end of the lead screw 302 to move deeper into the hollow center of the driven tip 301 and, conversely, that retracting the lead screw 302 into the drive hub 304 causes the distal end of the lead screw 302 to retract from the hollow center of the driven tip 301. As used herein, "extension" and "retraction" of the lead screw 302 from another structure or component means at least a small portion of the lead screw 302 enters or exits, as the case may be, for that structure or component. In the fully assembled state of arm 300, the distal end of lead screw 302 is always within the hollow center of the driven tip 301, and the proximal end of the lead screw 302 is always within the (threaded) hole 320 of the drive hub 304. How deep the lead screw 302 is within either the driven tip 301 and drive hub 304 varies according to the rotation angle of the arm 300 at any given point in time.

Figure 4:
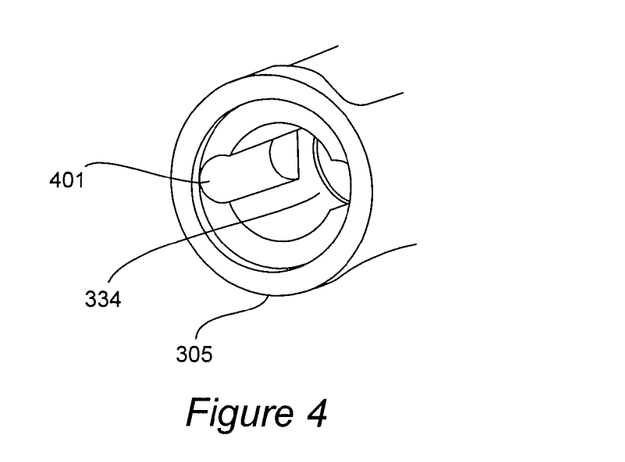
FIG. 4 is an enlarged view of the distal end of the housing of the rotating arm shown in FIG. 3.

Another function of the housing 305 is to prevent rotation of the drive pin 303 about the long axis of the arm 300. This is achieved via straight slots 401 in the inner walls of the housing 305. The straight slots 401 mate with the ends of the drive pin 303. The drive pin 303 has rounded or curved ends, as shown in FIG. 3, which increase load bearing capacity of the rotating arm. Alternatively, the drive pin 303 may have, for example, simple straight ends, this being a variation illustrated in FIGS. 8A-8C. FIG. 4 is a magnified view of straight slots 401 that mate with the drive pin 303 and the radial groove 334 that accepts the retaining ring 306.

As means for retaining the proximal portion of the driven tip 301 within the housing 305, the exemplary arm 300 includes the retaining ring 306. The driven tip 301 has a groove 333 and the housing 305 a groove 334, both of which are sized and positioned to receive the retaining ring 306 when the arm 300 is in the fully assembled state. In the assembled state, the retaining ring 306 prevents axial displacement between the driven tip 301 and the housing 305. Alternative means for providing such retentive functionality may occur to those of skill in the art in view of the teachings herein.

Figure 5:
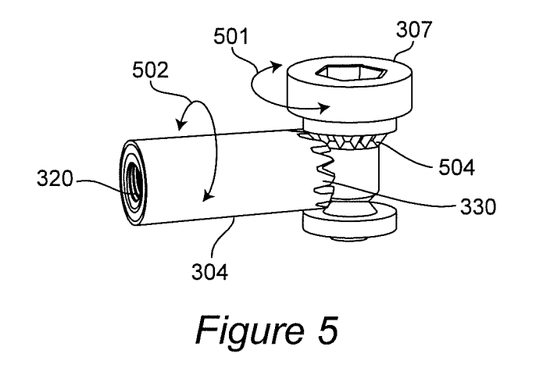
FIG. 5 shows the meshed gearings of the key hub and drive hub of the rotating arm shown in FIG. 3.
Figure 6:
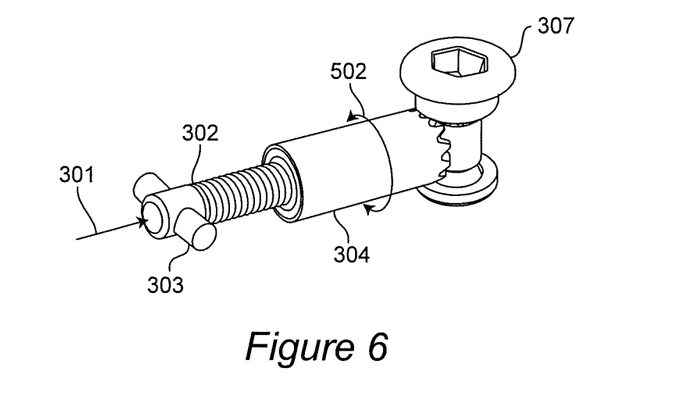
FIG. 6 shows the subassembly of key hub, drive hub, lead screw, and drive pin of the rotating arm shown in FIG. 3.
Figure 7:
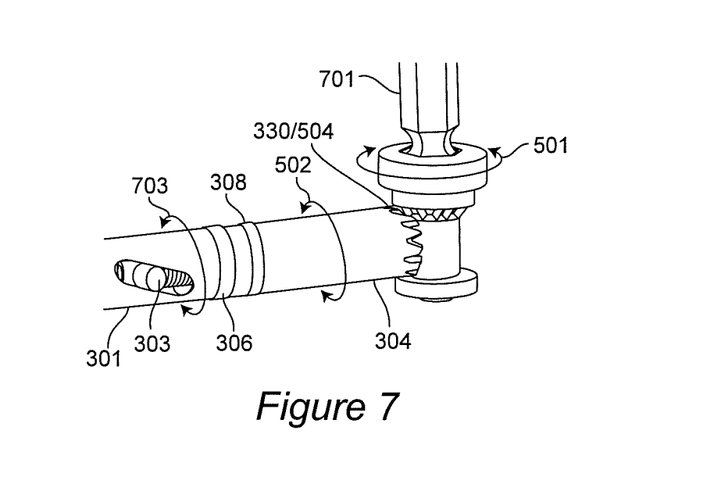
FIG. 7 shows the subassembly of key hub, drive hub, lead screw, drive pin, driven tip, and retaining ring of the rotating arm shown in FIG. 3.

Operation of the arm 300 will now be described with reference being made to FIGS. 5-7. In the fully assembled state, only two moving elements of the exemplary arm 300 are visible and accessible: namely, the driven tip 301 (more specifically, a distal portion thereof) and the key hub 307 (more specifically, the user interface of the key hub 307). An operator or user (e.g., a surgeon, not shown) actuates the user interface by, for example, applying a torque with a drive key 701 (e.g., an Allen wrench). Resulting rotation of the key hub 307 is indicated by arrow 501 in FIG. 5. This rotation may be clockwise or counterclockwise, each direction corresponding to one of either clockwise or counterclockwise rotation 502 of the drive hub 304 and, from there, clockwise or counterclockwise rotation 703 of the driven tip 301 and thereby the working end. The lead screw 302 and the threaded hole 320 of the drive hub 304 may be threaded left-handed or right-handed. Merely by convention, right-handed is usually preferred. In any case, the direction of the threading and helical slot(s) determines whether a clockwise rotation of the key hub 307 produces a clockwise or counterclockwise rotation of the driven tip 301. Rotation of the key hub 307 (or other user interface as prescribed by a particular embodiment) is transferred by meshed gearings 504 and 330 to the drive hub 304, producing rotation thereof about the long axis of the arm 300 (which, as previously indicated, is also the long axis of the drive hub 304 itself, these being coaxial).

Rotation of the drive hub 304 causes an extension or retraction of the lead screw 302 along the long axis of the arm 300, as described above. This extension/retraction is indicated by arrow 601. As may be appreciated by FIG. 6, in an absence of forces acting upon lead screw 302 and drive pin 303, a rotation 502 of the drive hub 304 could seemingly produce a rotation on lead screw 302 of equal amount, in which case no axial displacement (extension or retraction) would occur between the drive hub 304 and the lead screw 302. However, this scenario is prevented by the arrangement of drive pin 303 within straight slots 401 of the housing 305. As previously discussed, the straight slots 401 constrain the drive pin 303 to prevent its rotation about the long axis of the arm 300. Because the drive pin 303 passes through the lead screw 302, the lead screw is similarly constrained and prevented from rotation. As a result, a predetermined amount of rotation 502 of the drive hub 304 always produces a constant amount of extension or retraction of lead screw 302 which, in turn, produces a constant amount of rotation 703 to driven tip 301. The angle of rotation 703 of the driven tip 301, produced by a fixed amount of rotation 502 of the drive hub 304 (e.g., one degree), is configurable according to the design of a particular embodiment. For example, one parameter affecting this rotation ratio (i.e., degrees of rotation 502: degrees of rotation 703) that is selectable during manufacture is the pitch of the helical slots 313.

Extension or retraction 601 of lead screw 302, and therefore drive pin 303 (see FIG. 6), forces the drive pin 303 to bear against sides of the helical slots 313. The bearing forces produce a rotation 703 of the driven tip 301 along a pitch line of the helical slots 313. Rotation of the driven tip 301 is stepless and continuous, meaning that any angle of rotation is attainable. According to the exemplary embodiment of FIG. 3, the arm 300 is configured to be rotatable to any angle over a 35 degree range. Embodiments may be manufactured which have a still higher range limit (i.e., above 35 degrees, up to 90 degrees).

Figure 8A:
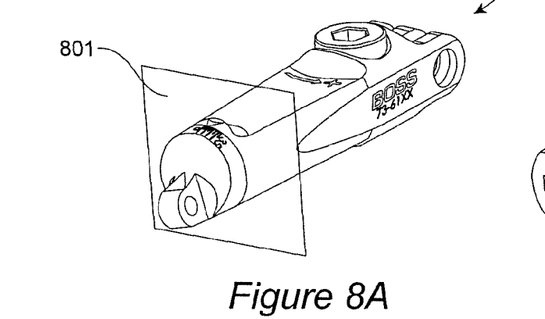
FIGS. 8A-8C show a cross section of a fully assembled rotating arm.
Figure 8B:
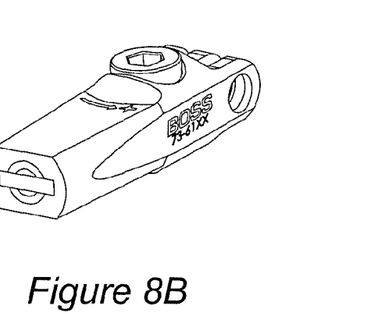
Figure 8C:
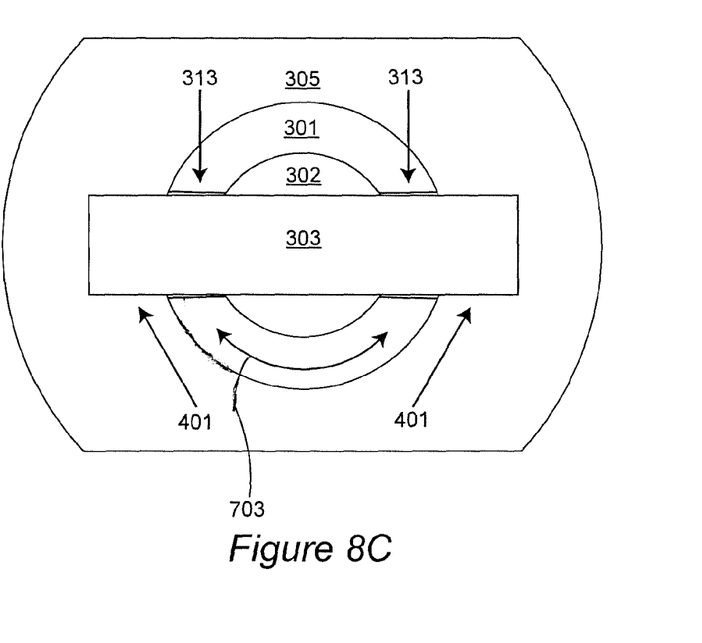

FIGS. 8A-8C illustrate a cross-section 801 of the arm 300 in a fully assembled state. Specifically, FIG. 8A shows the location where the cross-sectional view is taken, FIG. 8B shows the arm 300 with the distal portion to the cross-section 801 removed from view, and FIG. 8C shows an enlarged view of the components at the cross-section 801. The cross-section 801 is taken at the center of the drive pin. The straight slots 401 confine the drive pin 303 such that movement of the drive pin 303 is limited to axial displacement along long axis 309, e.g., into and out of the page for FIG. 8C. The driven tip 301 with the helical slots 313 is confined to rotation 703 (e.g., driven tip 301 cannot move into or out of the page in FIG. 8C). In FIG. 8C, it is apparent that the driven tip 301 is bound from any rotation that would be independent of the movement of other components. Rotation 703 of the driven tip 301 is only permitted to occur with the axial displacement of the drive pin 303. The drive pin 303 is moved by the lead screw 302 to travel linearly (i.e., into and out of the page in FIG. 8C) along the long axis 309 of the arm 300 (i.e., long axis of the concentric bores), allowing the driven tip 301 to rotate along the pitch line of its helical slots 313. This arrangement prevents forces applied to the working end from moving the internal components, thereby holding the desired amount of rotation (i.e., toe-in) without the need for additional locking mechanism(s) (e.g., a pawl or clamp).

Figure 9:
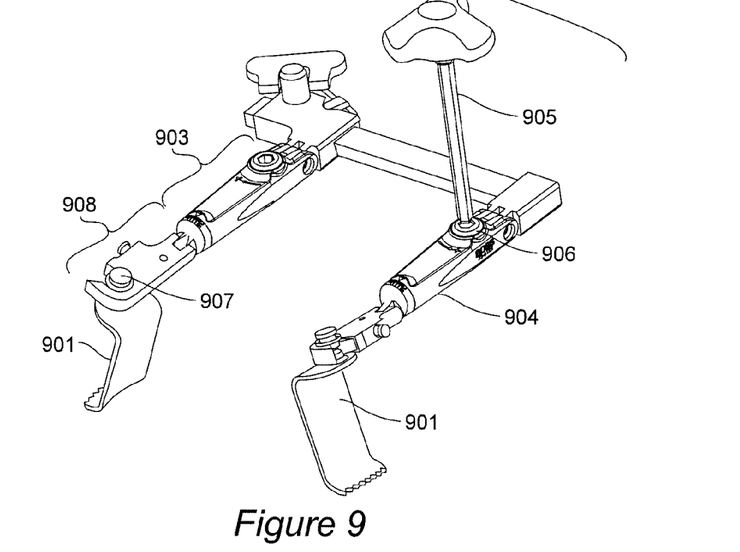
FIG. 9 shows a retractor with a plurality of rotating arms according to the invention.

FIG. 9 is a complete transverse retractor 900 with blades 901 attached as working ends. Retractor 900 includes a frame 902 and retractor arms 903 and 904. In the embodiment illustrated, both arms 903 and 904 are instances of a rotatable arm 300 as per the teachings herein. The arms 903 and 904 are actuated (i.e., made to have their driven tips rotated) using a drive key 905 which has an Allen wrench head that mates with the external user interface of the key hub 906. The working ends in this example embodiment are blades 901 together with blade hubs 907 and hub graspers 908, which are attached to the driven tips of the arms 903 and 904. Rotation of the driven tip of one of the arms rotates the working end attached to that respective arm.

Retractor embodiments according to the invention may use standard retractor frames such as frame 101 from FIG. 1. Alternatively, some embodiments may make use of other styles and sizes of frames, including frames not yet developed. A rotatable arm 300 is modular by design and thus highly versatile in this regard. The hinge points 332 and 312 at the proximal and distal ends, respectively, of an arm 300 may be customized for attachment to a particular type of frame or working end. The particular style of blades or other working end used, or specific surgical application, does not generally affect the applicability of a rotatable arm of the invention. "Working end", as used herein, generally refers to an instrument component that directly contacts tissues, as well as any hubs/attachment mechanisms specifically designed therefore. In the case of retractor blades, a working end generally includes the blade itself as well as a "grasper" and/or "blade hub". Holding open an incision is just one possible application of a working end. Another example is separation of bony tissue such as vertebrae.

Figure 10:
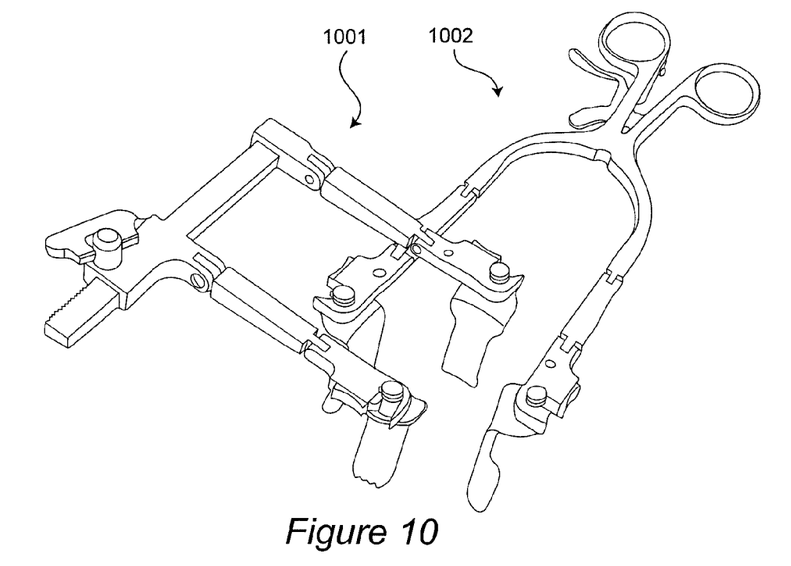
FIG. 10 shows two different retractors which may be modified to include a rotating arm according to the invention.

FIG. 10 shows a standard transverse retractor frame 1001 used in conjunction with a longitudinal frame 1002. The longitudinal frame can utilize a totally different mechanism for primary separation and holding of the tissue, such as a hinged scissors-like design with a curved ratchet and pawl mechanism. These and other retractor types may be modified by replacing one or more (e.g., all) of their respective arms with rotating arms (e.g., arm 300) according to the invention. Surgical retractors may have a total of one or more arms. The invention is not limited to just one style of retractor frame, surgical procedure, or application.

Figure 11:
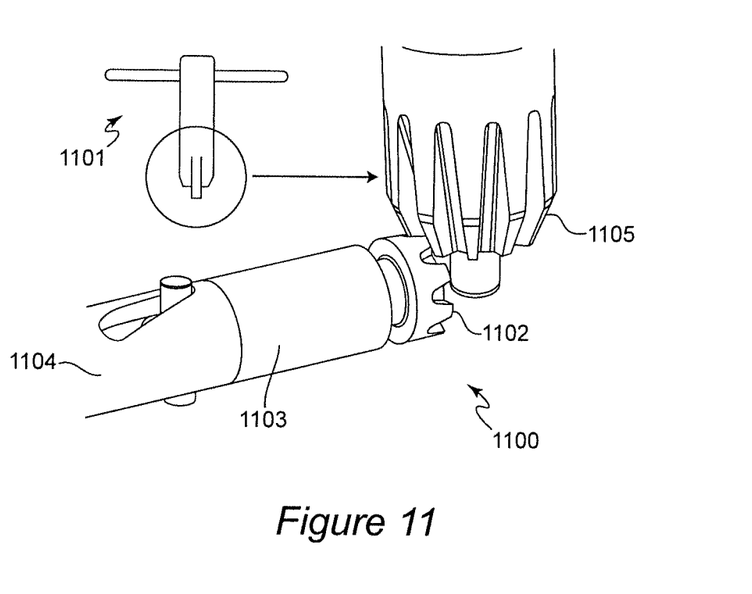
FIG. 11 shows an alternative user interface for actuating a drive hub of a rotating arm.

FIG. 11 shows an alternative subassembly 1100 within a rotating arm according to another embodiment. Subassembly 1100 primarily differs from the arrangement of components in arm 300 of FIG. 3 by a replacement of the key hub 307 with a Jacobs-style key 1101. The Jacobs-style key 1101 functions as both the drive key 701 and key hub 307 (including the key hub's gearing 504). The Jacobs-style key 1101 is inserted into the arm's housing to actuate the mechanism and turn the driven tip 1104. The bevel gear 1105 of the Jacobs-style key mesh with the gearing 1102 of the drive hub 1103.

Although the invention has been described in terms of exemplary embodiments and preferred features, those of skill the art will recognize that the invention is not limited by these embodiments and features and may be modified and practiced within the spirit and scope of the appended claims.

Having thus described my invention, what I claim as new and desire to secure by Letters Patent is:

1. A surgical retractor rotating arm, the rotating arm comprising:
   a driven tip having a distal portion connectable to a working end of the surgical retractor and a cylindrical proximal portion having opposing helical slots;

a lead screw having a distal end that is axially displaceable within a hollow longitudinal center of the proximal portion of the driven tip, the distal end of the lead screw transversely holding a drive pin with opposite portions disposed in the helical slots of the driven tip;

a cylindrical drive hub with gearing that, when driven, causes rotation of the drive hub about a center axis of the rotating arm, wherein a proximal end of the lead screw is arranged in a threaded hole of the drive hub, wherein a proximal end of the driven tip is axially connected to a distal end of the drive hub;

a retaining ring;

a housing that encloses the drive hub, the lead screw, the drive pin, and said proximal portion of the driven tip from an exterior environment; and a key hub with gearing that meshes with the gearing of the drive hub within the housing, the key hub having a user interface outside the housing, wherein actuation of the user interface by rotation of the key hub provides rotation of the drive hub via the meshed gearings, wherein rotation of the drive hub causes an extension or retraction of the lead screw along the center axis of the rotating arm, the extension or retraction forcing the drive pin to bear against sides of the helical slots and cause a rotation of the driven tip along a pitch line of the helical slots, wherein the gearing of the key hub and the gearing of the drive hub are meshed gears providing a change in operating angle, thereby changing an angle between input rotation provided by a user at the key hub, rotation of the drive hub, and output rotation at the working end, wherein the driven tip and the housing each have a groove for receiving the retaining ring which, after assembly, prevents axial displacement between the driven tip and the housing, wherein the housing prevents axial displacement between the driven tip and the drive hub, wherein the housing prevents rotation of the drive pin about the center axis of the rotating arm, and wherein the rotation of the driven tip rotates the working end of the surgical retractor.

2. The rotating arm of claim 1, wherein the drive pin has rounded or curved ends which increase load bearing capacity of the rotating arm.

3. The rotating arm of claim 1, further comprising a bearing spacer or thrust bearing between the proximal end of the driven tip and the distal end of the drive hub.

4. The rotating arm of claim 1, wherein the housing is of unitary construction.

5. The rotating arm of claim 1, wherein rotation of the driven tip is continuous and stepless.

6. The rotating arm of claim 1, wherein the housing is hermetically sealed to fully isolate the drive hub, the lead screw, the drive pin, and the proximal portion of the driven tip from an exterior environment.

7. A surgical retractor, comprising:

a frame;

one or more retractor arms, of which at least one retractor arm is a rotatable arm comprising:

a driven tip having a distal portion connectable to a working end of the surgical retractor and a cylindrical proximal portion having opposing helical slots;

a lead screw having a distal end that is axially displaceable within a hollow longitudinal center of the proximal portion of the driven tip, the distal end of the lead screw transversely holding a drive pin with opposite portions disposed in the helical slots of the driven tip;

a cylindrical drive hub with gearing that, when driven, causes rotation of the drive hub about a center axis of the rotating arm, wherein a proximal end of the lead screw is arranged in a threaded hole of the drive hub, wherein a proximal end of the driven tip is axially connected to a distal end of the drive hub;

a retaining ring;

a housing that encloses the drive hub, the lead screw, the drive pin, and said proximal portion of the driven tip; and a key hub with gearing that meshes with the gearing of the drive hub within the housing, the key hub having a user interface outside the housing, wherein actuation of the user interface by rotation of the key hub provides rotation of the drive hub via the meshed gearings, wherein rotation of the drive hub causes an extension or retraction of the lead screw along the center axis of the rotating arm, the extension or retraction forcing the drive pin to bear against sides of the helical slots and cause a rotation of the driven tip along a pitch line of the helical slots; and a working end attached to each of the one or more retractor arms, wherein the rotation of the driven tip of one arm of the one or more retractor arms rotates the working end attached to that arm, wherein the gearing of the key hub and the gearing of the drive hub are meshed gears providing a change in operating angle, thereby changing an angle between input rotation provided by a user at the key hub, rotation of the drive hub, and output rotation at the working end, wherein the driven tip and the housing each have a groove for receiving the retaining ring which, after assembly, prevents axial displacement between the driven tip and the housing, wherein the housing prevents axial displacement between the driven tip and the drive hub, and wherein the housing prevents rotation of the drive pin about the center axis of the rotating arm.

8. The surgical retractor of claim 7, wherein the drive pin has rounded or curved ends which increase load bearing capacity of the rotating arm.

9. The surgical retractor of claim 7, the rotating arm further comprising a bearing spacer or thrust bearing between the proximal end of the driven tip and the distal end of the drive hub.

10. The surgical retractor of claim 7, wherein the housing is of unitary construction.

11. The surgical retractor of claim 7, wherein rotation of the driven tip is continuous and stepless.

12. The surgical retractor of claim 7, wherein the housing is hermetically sealed to fully isolate the drive hub, the lead screw, the drive pin, and the proximal portion of the driven tip from an exterior environment.

* * * * *